US008859590B2

(12) United States Patent
Ghosh

(10) Patent No.: US 8,859,590 B2
(45) Date of Patent: Oct. 14, 2014

(54) INHIBITORS OF BACE1 AND METHODS FOR TREATING ALZHEIMER'S DISEASE

(75) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 281 days.

(21) Appl. No.: 13/132,665

(22) PCT Filed: Dec. 4, 2009

(86) PCT No.: PCT/US2009/066783
§ 371 (c)(1),
(2), (4) Date: Jun. 3, 2011

(87) PCT Pub. No.: WO2010/065861
PCT Pub. Date: Jun. 10, 2010

(65) Prior Publication Data
US 2011/0275619 A1 Nov. 10, 2011

Related U.S. Application Data

(60) Provisional application No. 61/120,174, filed on Dec. 5, 2008, provisional application No. 61/181,350, filed on May 27, 2009.

(51) Int. Cl.
| A61K 31/41 | (2006.01) |
| A61K 31/435 | (2006.01) |
| A61K 31/495 | (2006.01) |
| A61K 31/165 | (2006.01) |
| C07D 239/00 | (2006.01) |
| C07D 237/00 | (2006.01) |
| C07D 235/00 | (2006.01) |
| C07D 233/00 | (2006.01) |
| C07D 213/00 | (2006.01) |
| C07D 207/00 | (2006.01) |
| C07C 215/00 | (2006.01) |
| C07C 311/08 | (2006.01) |
| C07D 277/28 | (2006.01) |

(52) U.S. Cl.
CPC .......... *C07D 277/28* (2013.01); *C07C 2102/08* (2013.01); *C07C 311/08* (2013.01)
USPC ...... 514/330; 514/255.01; 514/423; 514/424; 514/522; 514/600; 514/605; 514/616; 544/226; 544/391; 548/538; 548/550; 564/79; 564/99; 564/153

(58) Field of Classification Search
USPC ......... 514/330, 423, 424, 522, 600, 605, 616; 548/538, 550; 544/226, 391; 564/79, 564/99, 153
See application file for complete search history.

(56) References Cited

U.S. PATENT DOCUMENTS

| 3,536,809 | A | 10/1970 | Applezwelg et al. |
| 3,598,123 | A | 8/1971 | Zaffaroni |
| 3,630,200 | A | 12/1971 | Higuchi |
| 3,847,770 | A | 11/1974 | Radlowe et al. |
| 3,916,899 | A | 11/1975 | Theeuwes et al. |
| 4,008,719 | A | 2/1977 | Theeuwes et al. |
| 4,687,610 | A | 8/1987 | Vassilatos |
| 4,769,027 | A | 9/1988 | Baker et al. |
| 5,059,595 | A | 10/1991 | Le Grazie |
| 5,073,543 | A | 12/1991 | Marshall et al. |
| 5,120,548 | A | 6/1992 | McCelland et al. |
| 5,354,566 | A | 10/1994 | Addesso et al. |
| 5,591,767 | A | 1/1997 | Mohr et al. |
| 5,627,165 | A | 5/1997 | Glazier |
| 5,639,476 | A | 6/1997 | Oshlack et al. |
| 5,674,533 | A | 10/1997 | Santus et al. |
| 5,733,566 | A | 3/1998 | Lewis |
| 7,291,620 | B2 * | 11/2007 | Coburn et al. ........... 514/255.01 |
| 7,348,356 | B2 | 3/2008 | Coburn et al. |
| 2006/0178383 | A1 | 8/2006 | Bischoff et al. |
| 2006/0229309 | A1 | 10/2006 | Thompson et al. |
| 2007/0213316 | A1 | 9/2007 | John et al. |
| 2007/0213331 | A1 | 9/2007 | Dally et al. |

FOREIGN PATENT DOCUMENTS

| WO | WO2006/103038 | 10/2006 |
| WO | WO 2007/058583 | 5/2007 |

OTHER PUBLICATIONS

A. K. Ghosh, et al., "Design of Potent Inhibitors for Human Brain Memapsin 2 (β-Secretase)," J. Am. Chem. Soc., 122:3522-3523 (2000).
L. Hong, et al., "Structure of the Protease Domain of Memapsin 2 (β-Secretase) Complexed with Inhibitor," Science, 290:150-153 (2000).
R. T. Turner III, et al., "Subsite Specificity of Memapsin 2 (β-Secretase): Implications for Inhibitor Design," Biochemistry, 40:10001-10006 (2001).
Arun K. Ghosh, et al., "Structure Based Design: Potent Inhibitors of Human Brain Memapsin 2 (β-Secretase)," J. Med. Chem., 44:2865-2868 (2001).
A. K. Ghosh, et al., "β-Secretase as a Therapeutic Target for Inhibitor Drugs," Curr. Med. Chem., 9:1135-1144 (2002).
Robert T. Turner, III, "Specificity of Memapsin 1 and Its Implications on the Design of Memapsin 2 (β-Secretase) Inhibitor Selectivity," Biochemistry, 41:8742-8746 (2002).

(Continued)

Primary Examiner — Kamal Saeed
Assistant Examiner — Janet L Coppins
(74) Attorney, Agent, or Firm — Purdue Research Foundation

(57) ABSTRACT

Inhibitors of BACE1 and compositions containing them are described. Use of the inhibitors and compositions containing them to treat Alzheimer's disease are described.

13 Claims, No Drawings

(56) References Cited

OTHER PUBLICATIONS

Lin Hong, et al., "Crystal Structure of Memapsin 2 (β-Secretase) in Complex with an Inhibitor OM00-3," Biochemistry, 41:10963-10967 (2002).

L. Hong, et al., "Memapsin 2 (β-Secretase) as a therapeutic target," Biochem. Soc. Trans, 30:530-534 (2002).

Jordan Tang, et al., "Study of Memapsin 2 (β-Secretase) and Strategy of Inhibitor Design," Journal of Molecular Neuroscience, 20:299-304 (2003).

G. Koelsch, et al., "Memapsin 2, a drug target for Alzheimer's disease," Biochemical Society Symposia, 70:213-220 (2003).

W.-P. Chang, et al., "In vivo inhibition of Aβ production by memapsin 2 (β-secretase) inhibitors," J. Neurochem., 89:1409-1416 (2004).

Robert T. Turner, III, et al., "Structural Locations and Functional Roles of New Subsites $S_5$, $S_6$ and $S_7$ in Memapsin 2 (β-Secretase)," Biochemistry, 44:105-112 (2005).

Gerald Koelsch, et al., "Analysis of Amyloid Precursor Protein Processing Protease β-Secretase: Tools for Memapsin 2 (β-Secretase) Inhibition Studies," Amyloid Precursor Protein 41-50 (2005).

Arun K. Ghosh, et al., "Structure-based design of cycloamide-urethane-derived novel inhibitors of human brain memapsin 2 (β-secretase)," Bioorg. Med. Chem. Lett., 15:15-20 (2005).

Arun K. Ghosh, et al., "Recent Development of Structure-Based β-Secretase Inhibitors for Alzheimer's Disease," Curr. Top. Med. Chem., 5:1609-1622 (2005).

Arun K. Ghosh, et al., "Design, Synthesis and X-ray Structure of Protein-Ligand Complexes: Important Insight into Selectivity of Memapsin 2 (β-Secretase) Inhibitors," J. Am. Chem. Soc., 128:5310-5311 (2006).

Arun K. Ghosh, et al., "Design, Synthesis and X-ray Structure of Potent Memapsin 2 (β-Secretase) Inhibitors with Isophthalamide Derivatives as the $P_2$-$P_3$-Ligands," J. Med. Chem., 50:2399-2407 (2007).

Arun K. Ghosh, et al., "Memapsin 2 (β-Secretase) Inhibitor Drug, between Fantasy and Reality," Curr. Alz. Res., 4:418-422 (2007).

Arun K. Ghosh, et al., "Potent memapsin 2 (beta-secretase) inhibitors: Design, synthesis, protein-ligand X-ray structure, and in vivo evaluation," Bioorg. Med. Chem. Lett., 18:1031-1036 (2008).

Arun K. Ghosh, et al., "Memapsin 2 (Beta-Secretase) Inhibitors: Drug Development," Curr. Alz. Res., 5:121-131 (2008).

Arun K. Ghosh, et al., "β-Secretase as a Therapeutic Target for Alzheimer's Disease," Neurotherapeutics, 5:399-408 (2008).

Polgar et al., "Virtual Screening for β-Secretase (BACE1) Inhibitors Reveals the Importance of Protonation States at Asp32 and Asp228," J. Med. Chem., 48:3749-3755 (2005).

PCT International Search Report/Written Opinion for PCT/US2009/066783, completed Apr. 6, 2010.

* cited by examiner

INHIBITORS OF BACE1 AND METHODS FOR TREATING ALZHEIMER'S DISEASE

CROSS-REFERENCE TO RELATED APPLICATIONS

This application is a U.S. national application under 37 C.F.R. & 371(b) of International Application Serial No. PCT/US2009/066783 filed Dec. 4, 2009, which claims the benefit of priority under 35 U.S.C. §119(e) to U.S. Provisional Application Ser. No. 61/120,174, filed on Dec. 5, 2008, and U.S. Provisional Application Ser. No. 61/181,350, filed on May 27, 2009. The entirety of the disclosure of each application is incorporated herein by reference

GOVERNMENT RIGHTS

This invention was made with government support under AG018933 awarded by the National Institutes of Health. The Government has certain rights in the invention.

BACKGROUND AND SUMMARY OF THE INVENTION

Alzheimer's disease is a progressive mental deterioration in a human resulting in loss of memory, confusion and disorientation, as well as, behavioral problems such as anxiety. Alzheimer's disease accounts for the majority of senile dementias and is a leading cause of death in adults. Currently-used treatments offer a small symptomatic benefit; however, no treatments to delay or halt the progression of the disease are as yet available.

The cause and progression of Alzheimer's disease are not well understood. Research indicates that the disease is associated with plaques and tangles in the brain. Histologically, the brains of persons afflicted with Alzheimer's disease are characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease and is a proteolytic fragment of amyloid precursor protein (APP). APP is cleaved initially by β-secretase (BACE1, also referred to as memapsin 2) followed by γ-secretase to generate Aβ. Without being bound by theory, it is believed that one approach to the treatment of Alzheimer's disease is to inhibit the production of Aβ.

It has been discovered that the compounds described herein are potent inhibitors of BACE1. It has also been discovered that those compounds may offer therapeutic benefits to patients suffering from or in need of relief from Alzheimer's disease. The compounds described herein include a substituted polyamine backbone core structure. Without being bound by theory, it is believed herein that the backbone core structure is capable of additional positive binding interactions with BACE1. Those additional interactions may be responsible at least in part for the observed activity and the therapeutic potential of the compounds described herein, and the compositions containing them.

In one illustrative embodiment of the invention described herein, compounds of the following formula are described herein:

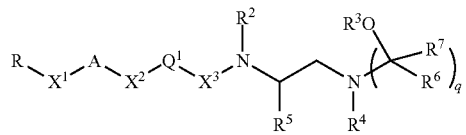

or a pharmaceutically acceptable salt thereof, wherein R, $X^1$, $X^2$, $X^3$, A, $Q^1$, $R^2$, $R^3$, $R^4$, $R^5$, $R^7$, and q are defined below.

In another illustrative embodiment, compounds of the following formula are described herein:

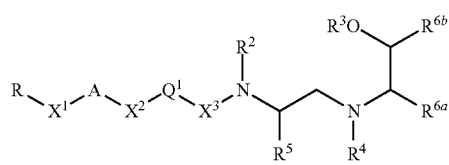

or a pharmaceutically acceptable salt thereof, wherein R, $X^1$, $X^2$, $X^3$, A, $Q^1$, $R^2$, $R^3$, $R^4$, $R^5$, $R^{6a}$, $R^{6b}$, $R^7$, and q are defined below.

In another illustrative embodiment, compounds of the following formula are described herein:

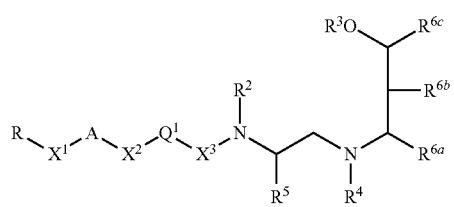

or a pharmaceutically acceptable salt thereof, wherein R, $X^1$, $X^2$, $X^3$, A, $Q^1$, $R^2$, $R^3$, $R^4$, $R^5$, $R^{6a}$, $R^{6b}$, $R^{6c}$, $R^7$, and q are defined below.

In addition, various genera and subgenera of each of R, $X^1$, $X^2$, $X^3$, A, $Q^1$, $R^2$, $R^3$, $R^4$, $R^5$, $R^{6a}$, $R^{6b}$, $R^{6c}$, $R^7$ and q are described herein. It is to be understood that all possible combinations of the various genera and subgenera of each of R, $X^1$, $X^2$, $X^3$, A, $Q^1$, $R^2$, $R^3$, $R^4$, $R^5$, $R^{6a}$, $R^{6b}$, $R^{6c}$, $R^7$, and q described herein represent additional illustrative embodiments of compounds of the invention described herein. It is to be further understood that each of those additional illustrative embodiments of compounds may be used in any of the compositions, methods, and/or uses described herein.

In another embodiment, compositions containing one or more of the compounds are also described herein. In one aspect, the compositions include a therapeutically effective amount of the one or more compounds for treating a patient with Alzheimer's disease. In another embodiment, methods for using the compounds and compositions for treating patients with Alzheimer's disease are also described herein. In one aspect, the methods include the step of administering one or more of the compounds and/or compositions containing them to a patient with Alzheimer's disease. In another aspect, the methods include administering a therapeutically effective amount of the one or more compounds and/or compositions for treating patients with Alzheimer's disease. In another embodiment, uses of the compounds and compositions in the manufacture of a medicament for treating patients with Alzheimer's disease are also described herein. In one aspect, the medicaments include a therapeutically effective amount of the one or more compounds and/or compositions for treating a patient with Alzheimer's disease.

It is appreciated herein that the compounds described herein may be used alone or in combination with other compounds useful for treating Alzheimer's disease, including those compounds that may operate by the same or different modes of action. In addition, it is appreciated herein that the compounds described herein may be used in combination with other compounds that are administered to treat other symptoms of Alzheimer's disease, such as compounds administered to improve cognitive function, that act as anxiolytics and/or antipsychotics to control behavior, and the like.

DETAILED DESCRIPTION

In one embodiment of the invention compounds of formula I

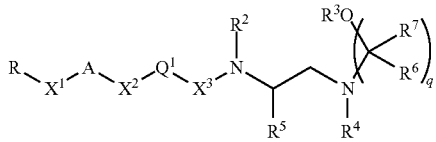

and pharmaceutically acceptable salts thereof are described; wherein

R is hydrogen, or alkyl, heteroalkyl, cycloalkyl, cycloheteroalkyl, aryl, or heteroaryl, each of which is optionally substituted;

$X^1$ is a bond or optionally substituted alkylene;

$X^2$ is a bond or $NR^1$, C(O), S(O), S(O)$_2$, $NR^1$—C(O), $NR^1$—S(O), $NR^1$—S(O)$_2$, optionally substituted alkylene, or optionally substituted alkylenoxy; where $R^1$ is independently selected in each instance from the group consisting of hydrogen, and alkyl, heteroalkyl, cycloalkyl, cycloheteroalkyl, aryl, arylalkyl, heteroaryl, and heteroarylalkyl, each of which is optionally substituted;

A is O or $NR^1$; or A is a nitrogen atom, and A and $X^1$ are taken together to form an optionally substituted heterocycle; or A and $X^2$ form an oxime;

$Q^1$ is a divalent carbocycle, heterocycle, unsaturated heterocycle, aryl, or heteroaryl, each of which is optionally substituted;

$X^3$ is C(O), S(O), S(O)$_2$ or $CHR^{13}$, where $R^{13}$ is hydrogen, or alkyl, heteroalkyl, cycloalkyl, cycloheteroalkyl, aryl, arylalkyl, heteroaryl, or heteroarylalkyl, each of which is optionally substituted;

$R^2$, $R^3$, and $R^4$ are in each instance independently selected from the group consisting of hydrogen and a prodrug forming group;

$R^5$ is alkyl, alkenyl, heteroalkyl, cycloalkyl, cycloheteroalkyl, aryl, arylalkyl, heteroaryl, or heteroarylalkyl, each of which is optionally substituted;

$R^6$ and $R^7$ are each in each instance independently selected from the group consisting of hydrogen, C(O)$R^8$, C(O)O$R^9$, C(O)$NR^{10a}R^{10b}$, S(O)$R^8$, S(O)$_2R^8$, S(O)$NR^{10a}R^{10b}$, S(O)$_2NR^{10a}R^{10b}$, and alkyl, alkenyl, heteroalkyl, cycloalkyl, cycloheteroalkyl, aryl, arylalkyl, heteroaryl, and heteroarylalkyl, each of which is optionally substituted; or $R^6$ and $R^7$ and any attached carbon atom form an optionally substituted carbocycle or heterocycle;

$R^8$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted; and $R^9$ is in each instance independently selected from the group consisting of hydrogen, and alkyl, alkenyl, heteroalkyl, cycloalkyl, cycloheteroalkyl, aryl, arylalkyl, heteroaryl, and heteroarylalkyl, each of which is optionally substituted;

$R^{10a}$ and $R^{10b}$ are in each instance independently selected from the group consisting of hydrogen, and alkyl, alkenyl, heteroalkyl, cycloalkyl, cycloheteroalkyl, aryl, arylalkyl, heteroaryl, heteroarylalkyl, alkylsulfonyl, and arylsulfonyl, each of which is optionally substituted; or $R^9$ and $R^{10}$ and the attached nitrogen form an optionally substituted heterocycle; and q is 2, 3, or 4.

In another embodiment, compounds of formula I and pharmaceutically acceptable salts thereof are described; wherein R is hydrogen, alkyl, heteroalkyl, haloalkyl, cycloalkyl, heterocycloalkyl, aryl, arylalkyl, heteroaryl, or heteroarylalkyl, each of which is optionally substituted;

$Q^1$ is cycloalkylene, heterocycloalkylene, arylene, or heteroarylene, each of which is optionally substituted;

$X^1$ is a bond or optionally substituted alkylene;

$X^2$ is —C(O)—, —S(O)$_p$—, or optionally substituted alkylene;

$X^3$ is —C(O)— or —S(O)$_p$—;

A is O or $NR^1$; where $R^1$ is hydrogen, alkyl, heteroalkyl, haloalkyl, cycloalkyl, heterocycloalkyl, aryl, arylalkyl, heteroaryl, or heteroarylalkyl, each of which is optionally substituted, or $R^1$ and $X^1$ together with the attached nitrogen form an optionally substituted heterocycle;

p is in each instance independently selected from the group consisting of 1 and 2;

q is 2, 3, or 4;

$R^2$, $R^3$, and $R^4$ are in each instance independently selected from the group consisting of hydrogen and a prodrug forming group;

$R^5$ is alkyl, alkenyl, heteroalkyl, haloalkyl, cycloalkyl, heterocycloalkyl, aryl, arylalkyl, heteroaryl, or heteroarylalkyl, each of which is optionally substituted;

$R^6$ and $R^7$ are each in each instance independently selected from the group consisting of hydrogen, ketones, such as C(O)$R^8$, carboxylic acids and derivatives thereof, such as C(O)O$R^9$, C(O)$NR^{10a}R^{10b}$, and alkyl, alkenyl, heteroalkyl, haloalkyl, cycloalkyl, heterocycloalkyl, aryl, arylalkyl, heteroaryl, and heteroarylalkyl, each of which is optionally substituted, or any one of $R^6$ and $R^7$ and the attached carbons are taken together to form an optionally substituted carbocycle or heterocycle, including bicyclic carbocycles, heterocycles, and aryls;

$R^8$ and $R^9$ are in each instance independently selected from the group consisting of alkyl, alkenyl, heteroalkyl, haloalkyl, cycloalkyl, heterocycloalkyl, aryl, arylalkyl, heteroaryl, and heteroarylalkyl, each of which is optionally substituted; and $R^{10a}$ and $R^{10b}$ are in each instance independently selected from the group consisting of hydrogen, and alkyl, alkenyl, heteroalkyl, haloalkyl, cycloalkyl, heterocycloalkyl, aryl, arylalkyl, heteroaryl, alkylsulfonyl, arylsulfonyl, and heteroarylalkyl, each of which is optionally substituted; or $R^9$ and $R^{10}$ are taken together with the attached nitrogen to form an optionally substituted heterocycle.

In another embodiment, the compounds of the preceding embodiments wherein q is 2 are described. In yet another embodiment, the compounds of the prior embodiments wherein q is 3 are described.

In another embodiment, compounds of formula II

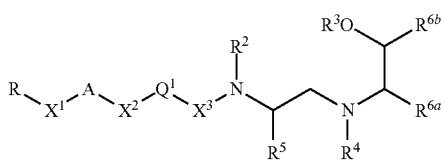

and pharmaceutically acceptable salts thereof are described; wherein
$R^{6a}$ and $R^{6b}$ are each independently selected from the group consisting of hydrogen, $C(O)R^8$, $C(O)OR^9$, $C(O)NR^{10a}R^{10b}$, $S(O)R^8$, $S(O)_2R^8$, $S(O)NR^{10a}R^{10b}$, $S(O)_2NR^{10a}R^{10b}$, and alkyl, alkenyl, heteroalkyl, cycloalkyl, cycloheteroalkyl, aryl, arylalkyl, heteroaryl, and heteroarylalkyl, each of which is optionally substituted; or $R^{6a}$ and $R^{6b}$ and the attached carbons form an optionally substituted carbocycle or heterocycle.

In another embodiment, compounds of formula III

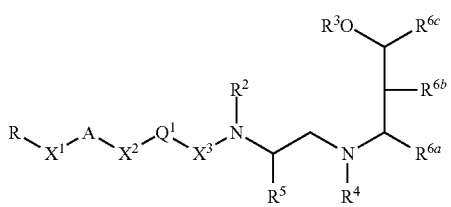

and pharmaceutically acceptable salts thereof are described; wherein
$R^{6a}$, $R^{6b}$, and $R^{6c}$ are each independently selected from the group consisting of hydrogen, $C(O)R^8$, $C(O)OR^9$, $C(O)NR^{10a}R^{10b}$, $S(O)R^8$, $S(O)_2R^8$, $S(O)NR^{10a}R^{10b}$, $S(O)_2NR^{10a}R^{10b}$, and alkyl, alkenyl, heteroalkyl, cycloalkyl, cycloheteroalkyl, aryl, arylalkyl, heteroaryl, and heteroarylalkyl, each of which is optionally substituted; or $R^{6b}$ and $R^{6c}$ and the attached carbons form an optionally substituted carbocycle or heterocycle.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

In another embodiment, the compound of formula I wherein at least one of $R^7$ is alkyl and at least one of $R^6$ is $C(O)NR^{10a}R^{10b}$ or $CH_2NR^{10a}R^{10b}$ is described.

In another embodiment, the compounds described in any of the preceding embodiments wherein one of $R^6$ is

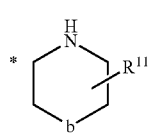

wherein * denotes the point of attachment; b is O, $S(O)_m$, or $NR^{12}$, where m is 0, 1, or 2;
$R^{11}$ represents from 1 to 4 substituents independently in each instance selected from the group consisting of hydrogen, and alkyl, alkenyl, heteroalkyl, cycloalkyl, heterocycloalkyl, aryl, arylalkyl, heteroaryl, and heteroarylalkyl, each of which is optionally substituted; and
$R^{12}$ is hydrogen, or alkyl, alkenyl, heteroalkyl, $OR^8$, $C(O)R^8$, $C(O)OR^8$, $C(O)NR^9R^{10}$, alkylsulfonyl, arylsulfonyl, cycloalkyl, heterocycloalkyl, aryl, arylalkyl, heteroaryl, and heteroarylalkyl, each of which is optionally substituted.

In another embodiment, the compound of formulae II is described wherein $R^{6a}$ is

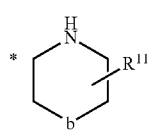

wherein * denotes the point of attachment; and b is a bond, $CH_2$, O, S, S(O) $S(O)_2$, or $NR^{12}$.

In another embodiment, the compound wherein $R^{11}$ represents from 1 to 4 substituents selected independently in each instance from the group consisting of hydrogen, alkyl, alkenyl, heteroalkyl, haloalkyl, cycloalkyl, heterocycloalkyl, aryl, arylalkyl, heteroaryl, and heteroarylalkyl, each of which is optionally substituted; and
$R^{12}$ is hydrogen, or alkyl, alkenyl, heteroalkyl, haloalkyl, $OR^8$, $C(O)R^8$, $C(O)OR^8$, $C(O)NR^9R^{10}$, alkylsulfonyl, arylsulfonyl, cycloalkyl, heterocycloalkyl, aryl, arylalkyl, heteroaryl, or heteroarylalkyl, each of which is optionally substituted is described.

In another embodiment, the compound described in any preceding embodiment wherein $R^{11}$ represents from 1 to 2 substituents selected independently in each instance from the group consisting of hydrogen, alkyl, alkenyl, heteroalkyl, haloalkyl, cycloalkyl, heterocycloalkyl, aryl, arylalkyl, heteroaryl, and heteroarylalkyl, each of which is optionally substituted are described.

In another embodiment, the compounds described in any one of the preceding embodiments wherein $R^{11}$ represents a substituent selected from the group consisting of hydrogen, alkyl, alkenyl, heteroalkyl, haloalkyl, cycloalkyl, heterocycloalkyl, aryl, arylalkyl, heteroaryl, and heteroarylalkyl, each of which is optionally substituted are described.

In another embodiment, the compound of formulae II is described wherein at least one of $R^6$ is

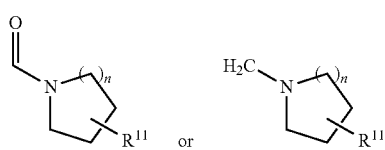

where n is 0, 1, 2, or 3.

In another embodiment, the compound of formulae II is described wherein $R^{6a}$ is C(O)NHR$^{10a}$, where $R^{10a}$ is alkyl; and $R^{6b}$ is alkyl.

In another embodiment, the compound of formulae II is described wherein $R^{6a}$ is C(O)NHR$^{10a}$, where $R^{10a}$ is optionally substituted arylalkyl; and $R^{6b}$ is alkyl.

In another embodiment, the compound of formulae II is described wherein $R^{6a}$ is optionally substituted benzyl; and $R^{6b}$ is hydrogen.

In another embodiment, the compound of formulae II is described wherein $R^{6a}$ is C(O)OR$^9$, C(O)NR$^{10a}$R$^{10b}$ or; and CH$_2$NR$^9$R$^{10}$; $R^{6b}$ is alkyl, heteroalkyl, aryl, or arylalkyl, each of which is optionally substituted.

In another embodiment, the compound of formulae II is described wherein $R^{6a}$ is optionally substituted aryl; and $R^{6b}$ is alkyl, heteroalkyl, aryl, or arylalkyl, each of which is optionally substituted.

In another embodiment, the compound of formulae II is described wherein $R^{6a}$ is optionally substituted aminoalkyl; and $R^{6b}$ is alkyl, heteroalkyl, aryl, or arylalkyl, each of which is optionally substituted.

In another embodiment, the compound of formulae II is described wherein $R^{6a}$ is alkylaminoalkyl; and $R^{6b}$ is alkyl, heteroalkyl, aryl, or arylalkyl, each of which is optionally substituted.

In another embodiment, the compound of formulae II is described wherein $R^{6a}$ is CH$_2$NHR$^{10a}$; where $R^{10a}$ is optionally branched alkyl.

In another embodiment, the compound of formulae II is described wherein $R^{6a}$ is CH$_2$NHR$^{10a}$; where NR$^{10a}$R$^{10b}$ is an amino acid residue.

In another embodiment, the compound of formulae II is described wherein the amino acid is a naturally occurring amino acid, or stereoisomer thereof.

In another embodiment, the compound of formulae II is described wherein the amino acid is a naturally occurring amino acid.

In another embodiment, the compound of formulae II is described wherein $R^{6a}$ is CH$_2$NR$^{10a}$R$^{10b}$; where NR$^{10a}$R$^{10b}$ is a descarboxy amino acid residue.

In another embodiment, the compound of formulae II is described wherein NR$^{10a}$R$^{10b}$ is descarboxy phenylalaninyl, which is optionally substituted.

In another embodiment, the compound of formulae II is described wherein NR$^{10a}$R$^{10b}$ is descarboxy valinyl.

In another embodiment, the compound of formulae II is described wherein $R^{6a}$ is C(O)NR$^{10a}$R$^{10b}$; where NR$^{10a}$R$^{10b}$ is an amino acid residue.

In another embodiment, the compound of formulae II is described wherein the amino acid is a naturally occurring amino acid, or stereoisomer thereof.

In another embodiment, the compound of formulae II is described wherein $R^{6a}$ is C(O)NR$^{10a}$R$^{10b}$; where NR$^{10a}$R$^{10b}$ is a descarboxy amino acid residue.

In another embodiment, the compound of formulae II is described wherein the amino acid is a naturally occurring amino acid.

In another embodiment, the compound of formulae II is described wherein NR$^{10a}$R$^{10b}$ is descarboxy phenylalaninyl, which is optionally substituted.

In another embodiment, the compound of formulae II is described wherein NR$^{10a}$R$^{10b}$ is descarboxy valinyl.

In another embodiment, the compound of formulae II is described where $R^{6a}$, $R^{6b}$, and the attached carbons form optionally substituted indane.

In another embodiment, the compound of formulae II is described where $R^{6a}$, $R^{6b}$, and the attached carbons form optionally substituted indane.

In another embodiment, the compound of formulae II is described wherein $R^{6b}$ is heteroalkyl.

In another embodiment, the compound of formulae III is described wherein $R^{6b}$, $R^{6c}$, and the attached carbons form a carbocycle.

In another embodiment, the compound of formulae III is described wherein $R^{6a}$ is C(O)NR$^{10a}$R$^{10b}$; and $R^{6b}$, $R^{6c}$ and the attached carbons form a carbocycle.

In another embodiment, the compound described in any of the preceding embodiments wherein $X^1$ is methylene or substituted methylene is described.

In another embodiment, the compound described in any of the preceding embodiments wherein $X^2$ is C(O), S(O), S(O)$_2$, or optionally substituted alkylene is described.

In another embodiment, the compound described in any of the preceding embodiments wherein $Q^1$ is a divalent carbocycle, heterocycle, aryl, or heteroaryl, each of which is optionally substituted is described.

In another embodiment, the compound described in any of the preceding embodiments wherein $X^3$ is C(O), S(O), or S(O)$_2$ is described.

In another embodiment, the compound of any preceding embodiment wherein $R^1$ and $X^1$ are together with the attached nitrogen to form an optionally substituted heterocycle is described.

In another embodiment, the compounds described in any one of the preceding embodiments wherein A is NR$^1$, R is heteroaryl, and $R^1$, $X^1$ and the attached nitrogen form a heterocycle are described.

In another embodiment, the compound described in any one of the preceding embodiments wherein A is NR$^1$, $R^1$ is hydrogen, $X^1$ is a bond, $X^2$ is C(O), and R is optionally substituted arylalkyl is described In another embodiment, the compound described in any one of the preceding embodiments wherein A is NR$^1$, $R^1$ is hydrogen, $X^1$ is a bond, $X^2$ is C(O), and R is (R)-1-phenyl-1-ethyl is described.

In another embodiment, the compound described in any of the preceding embodiments wherein $R^6$ and $R^7$ are each in each instance independently selected from the group consisting of hydrogen, C(O)R$^8$, C(O)OR$^9$, C(O)NR$^{10a}$R$^{10b}$, and alkyl, alkenyl, heteroalkyl, cycloalkyl, cycloheteroalkyl, aryl, arylalkyl, heteroaryl, and heteroarylalkyl, each of which is optionally substituted; or one of $R^6$ and one of $R^7$ and any attached carbon form an optionally substituted carbocycle or heterocycle is described.

In another embodiment, the compound of any of the embodiments described herein wherein one or more of R, $R^1$, $R^5$, $R^6$, $R^7$, $R^8$, $R^9$, $R^{10a}$, $R^{10b}$, $R^{11}$ or $R^{13}$ is haloalkyl is described.

In another embodiment, the compound described in any of the preceding embodiments wherein $Q^1$ is 1,3-phenylene, 2,6-pyridylene, 2,4-pyridylene, or 3,5-pyridylene, each of which is optionally substituted is described.

In another embodiment, the compound described in any of the preceding embodiments wherein $Q^1$ is 1,3-phenylene, 2,4-pyridylene, or 3,5-pyridylene, each optionally substituted with from 1 to three substituents independently selected in each instance from the group consisting of halogen, NR$^{10a}$R$^{10b}$, OR$^9$, C(O)R$^8$, C(O)NR$^{10a}$R$^{10b}$, C(O)OR$^9$, S(O)$_m$R$^8$, where m is in each instance independently selected from 0, 1 or 2; and alkyl, heteroalkyl, cycloalkyl, alkenyl, aryl, arylalkyl, heteroaryl and heteroarylalkyl, each of which is optionally substituted is described. In another embodiment, at least one substituent is haloalkyl.

In another embodiment, the compound described in any of the preceding embodiments wherein at least one substituent is $R^{10a}R^{10b}$N-alkyl or $R^9$O-alkyl is described.

In another embodiment, the compound described in any of the preceding embodiments wherein $Q^1$ is 1,3-phenylene, 2,4-pyridylene, or 3,5-pyridylene, substituted with alkylamino alkylsulfonamide is described.

In another embodiment, the compound described in any of the preceding embodiments wherein $Q^1$ is 1,3-phenylene, 2,4-pyridylene, or 3,5-pyridylene, substituted with 1,2-isothiazolidines-1,1-dioxide or tetrahydro-2H-thiazine-1,1-dione is described.

In another embodiment, the compound described in any of the preceding embodiments wherein $Q^1$ is 1,3-phenylene, 2,4-pyridylene, or 3,5-pyridylene, substituted with pyrrolidinone or piperidinone is described.

In another embodiment, the compound described in any of the preceding embodiments wherein $Q^1$ is 1,3-phenylene is described.

In another embodiment, the compound described in any of the preceding embodiments wherein $X^2$ and $X^3$ are C(O) is described.

In another embodiment, the compound described in any of the preceding embodiments wherein $A$-$X^2$ is amino or aminoalkyl; and $X^3$ is C(O) is described.

In another embodiment, the compound described in any of the preceding embodiments wherein $R^5$ is optionally substituted arylalkyl is described.

In another embodiment, the compound described in any of the preceding embodiments wherein $R^5$ is substituted arylalkyl, provided that at least one substituent is fluoro is described.

In another embodiment, the compound described in any of the preceding embodiments wherein $R^5$ is 3,5-difluorobenzyl is described.

In another embodiment, the compound described in any of the preceding embodiments wherein $R^5$ is alkyl is described.

In another embodiment, the compound described in any of the preceding embodiments wherein $R^5$ is branched alkyl is described.

In another embodiment, the compound described in any of the preceding embodiments wherein R is optionally substituted heteroaryl, $X^1$ is $CH_2$, A is $NR^1$, and $R^1$ is hydrogen or alkyl is described.

In another embodiment, the compound described in any of the preceding embodiments wherein the heteroaryl is optionally substituted oxazolyl or thiazolyl is described.

In another embodiment, the compound described in any of the preceding embodiments wherein the heteroaryl is substituted oxazolyl or thiazolyl is described.

In another embodiment, the compound described in any of the preceding embodiments wherein $R^1$ is alkyl is described.

In another embodiment, the compound described in any of the preceding embodiments wherein R is optionally substituted aryl and $X^1$ is alkylene is described.

In another embodiment, the compound described in any of the preceding embodiments wherein R is substituted aryl, where at least one substituent is fluoro; and $X^1$ is alkylene is described.

In another embodiment, the compound described in any of the preceding embodiments wherein R is optionally substituted aryl, $X^1$ is optionally substituted alkylene, and A is $NR^1$, where $R^1$ is hydrogen or alkyl is described.

In another embodiment, the compound described in any of the preceding embodiments wherein R is optionally substituted aryl, $X^1$ is optionally substituted alkylene, A is $NR^1$, where $R^1$ is hydrogen, and $X^2$ is C(O) is described.

In another embodiment, the compound described in any of the preceding embodiments wherein R is aryl, $X^1$ is alkylene, A is $NR^1$, where $R^1$ is hydrogen, and $X^2$ is C(O) is described.

In another embodiment, the compound described in any of the preceding embodiments wherein A is a nitrogen atom, and A and $X^1$ are taken together to form an optionally substituted heterocycle is described.

In another embodiment, the compound described in any of the preceding embodiments wherein the heterocycle is pyrrolidinyl is described.

In another embodiment, the compound described in any of the preceding embodiments wherein the heterocycle is pyrrolidinyl, and R is alkyl, heteroalkyl, or heteroaryl, each of which is optionally substituted is described.

In another embodiment, the compound described in any of the preceding embodiments wherein the heterocycle is pyrrolidinyl, and R is alkyl, alkoxyalkyl, or aminoalkyl is described.

In another embodiment, the compound described in any of the preceding embodiments wherein A is a nitrogen atom, and A and $X^1$ are taken together to form a heterocycle, and R is heteroaryl is described.

In another embodiment, the compound described in any of the preceding embodiments wherein R and $X^1$ form phenyleth-2-yl; A is $NR^1$, where $R^1$ is hydrogen, and $X^2$ is C(O) is described.

In another embodiment, the compound described in any of the preceding embodiments wherein $R^3$ is hydrogen is described.

In another embodiment, the compound described in any of the preceding embodiments wherein $R^7$ in each instance is hydrogen is described.

In another embodiment, the compound described in any of the preceding embodiments wherein $R^{12}$ is haloalkyl is described.

In another embodiment, the compound described in any of the preceding embodiments wherein b is O, S. S(O), $S(O)_2$, or $NR^{12}$ is described.

In another embodiment, the compound described in any of the preceding embodiments wherein $R^{11}$ is optionally substituted arylalkyl is described.

In another embodiment, the compound described in any of the preceding embodiments wherein $R^6$ and $R^7$ are each in each instance independently selected from the group consisting of hydrogen, ketones, such as $C(O)R^8$, carboxylic acids and derivatives thereof, such as $C(O)OR^8$, $C(O)NR^9R^{10}$, and alkyl, alkenyl, heteroalkyl, haloalkyl, cycloalkyl, heterocycloalkyl, aryl, arylalkyl, heteroaryl, and heteroarylalkyl, each of which is optionally substituted, or any one of $R^6$ and $R^7$ and the attached carbons are taken together to form an optionally substituted carbocycle or heterocycle, including bicyclic carbocycles, heterocycles, and aryls is described.

In another embodiment, the compounds described in any of the preceding embodiments wherein one of $R^6$ is

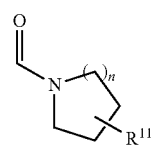

where n is 0, 1, 2, or 3 are described.

In another embodiment, the compounds described in any of the preceding embodiments wherein one of $R^6$ is

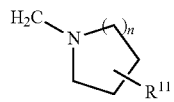

where n is 0, 1, 2, or 3 are described.

In another embodiment, a pharmaceutical composition comprising any of the compounds described herein, in a therapeutically effective amount for treating Alzheimer's disease, and one or more of a carrier, diluent, or excipient therefor is described.

In another embodiment, a method for treating a patient in need of relief from Alzheimer's disease, the method comprising the step of administering to the patient a therapeutically effective amount of one or more of the compounds described herein, or a pharmaceutical composition thereof, where the pharmaceutical composition includes one or more carriers, diluents, or excipients, or a combination thereof is described.

In another embodiment, use of one or more of the compounds described herein, or a pharmaceutical composition thereof, in the manufacture of a medicament for treating Alzheimer's disease, where the pharmaceutical composition includes one or more carriers, diluents, or excipients, or a combination thereof; and where the medicament and the pharmaceutical composition each comprise a therapeutically effective amount of the compound or compounds is described.

In another embodiment, the compounds described in any of the preceding embodiments wherein one of $R^{11}$ is arylalkyl are described.

In another illustrative embodiment, the following compounds are described

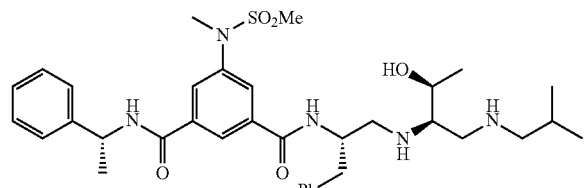

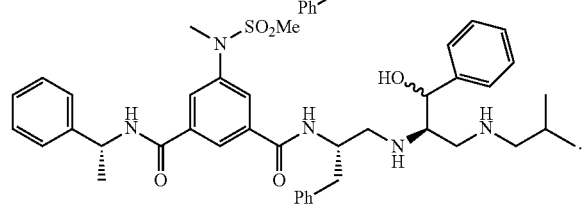

In another illustrative embodiment, the following compounds are described

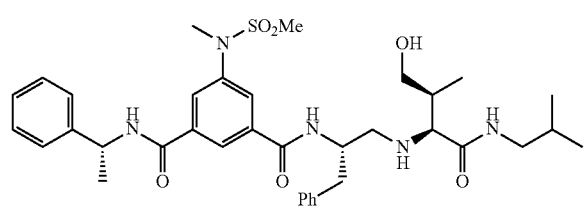

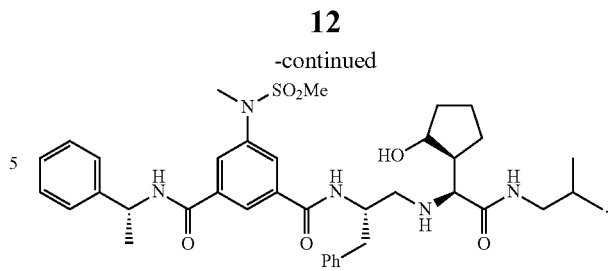

In another illustrative embodiment, the following compounds are described

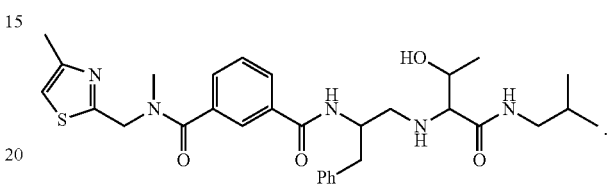

In another illustrative embodiment, the following illustrative examples of the compounds are described

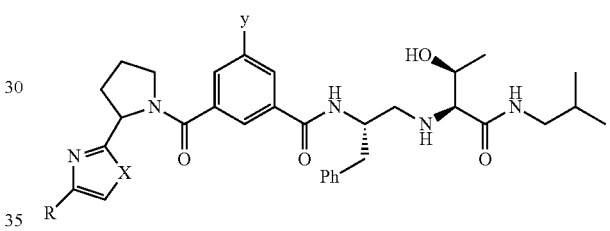

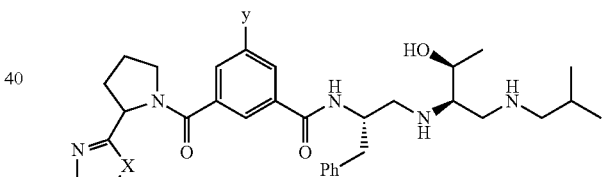

wherein X is O, S, or NMe; R is hydrogen, alkyl, or heteroalkyl; and y is hydrogen, alkyl, or heteroalkyl. In another illustrative embodiment, the following illustrative examples of the compounds are described

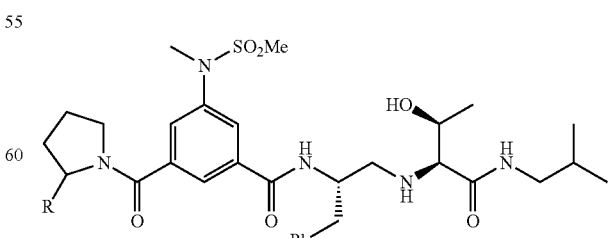

wherein R is alkyl or heteroalkyl, including but not limited to an ether, amino, or hydroxyalkyl.

In another illustrative embodiment, the following compounds are described

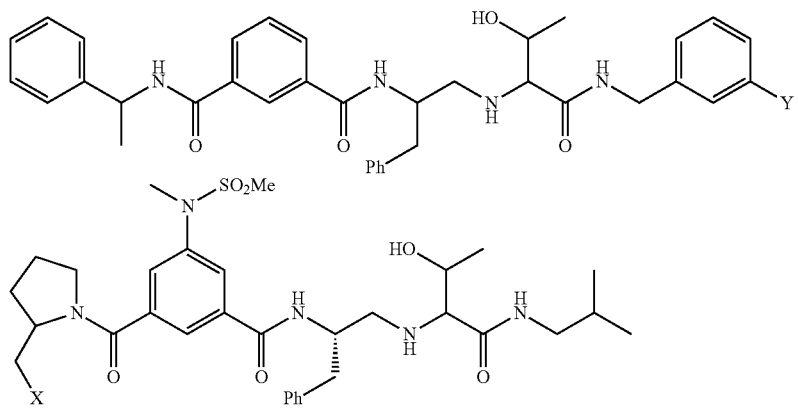

wherein X is OMe, NHMe, alkyl, hydroxyalkyl, or heteroalkyl; and Y is OMe, NHMe, alkyl, hydroxyalkyl, or heteroalkyl.

In another embodiment, the following illustrative examples of the compounds are described

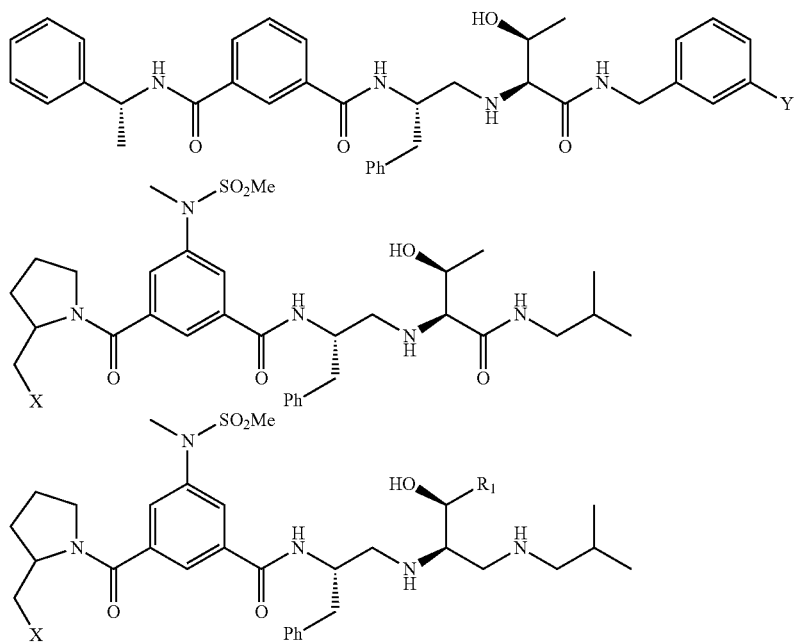

wherein Y is OMe, NHMe, alkyl, hydroxyalkyl, or heteroalkyl; and X is OMe, NHMe, alkyl, hydroxyalkyl, or heteroalkyl.

In another illustrative embodiment, the following compounds are described

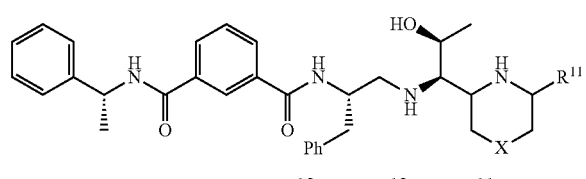

wherein X is O, $SO_2$, or $NR^{12}$; and $R^{12}$ and $R^{11}$ are each independently hydrogen, alkyl, or heteroalkyl.

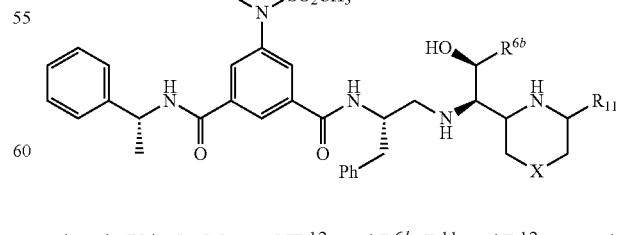

wherein X is O, $SO_2$, or $NR^{12}$; and $R^{6b}$, $R^{11}$ and $R^{12}$ are each independently hydrogen, alkyl, or heteroalkyl.

In another illustrative embodiment, the following compounds are described

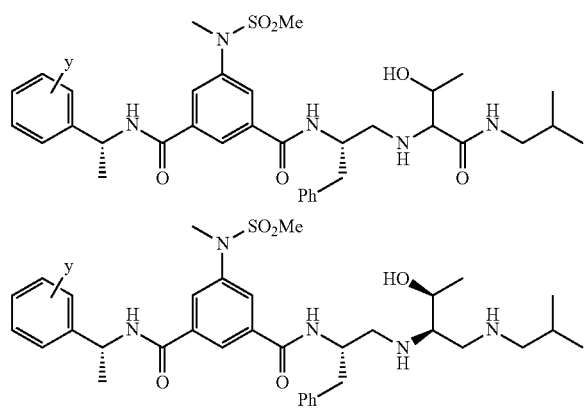

wherein y is OMe, NHMe, alkyl, hydroxyalkyl, heteroalkyl, or halo, such as fluoro.

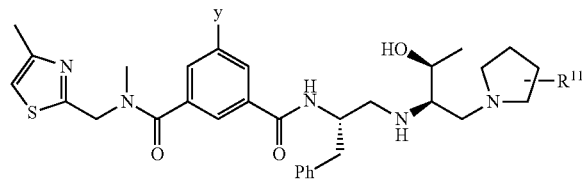

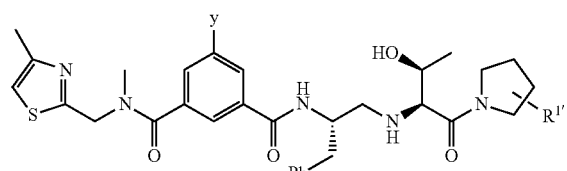

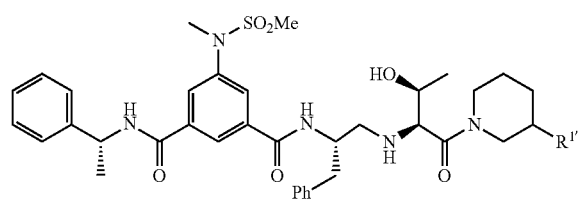

wherein $R^{11}$ is OMe, NHMe, alkyl, hydroxyalkyl, or heteroalkyl; and y is hydrogen, alkyl, or heteroalkyl.

In another illustrative embodiment, the following compounds are described

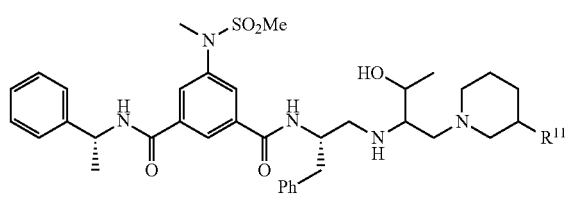

wherein $R^{11}$ is OMe, NHMe, alkyl, hydroxyalkyl, or heteroalkyl; and y is hydrogen, alkyl, or heteroalkyl.

In another illustrative embodiment, compounds of formulae

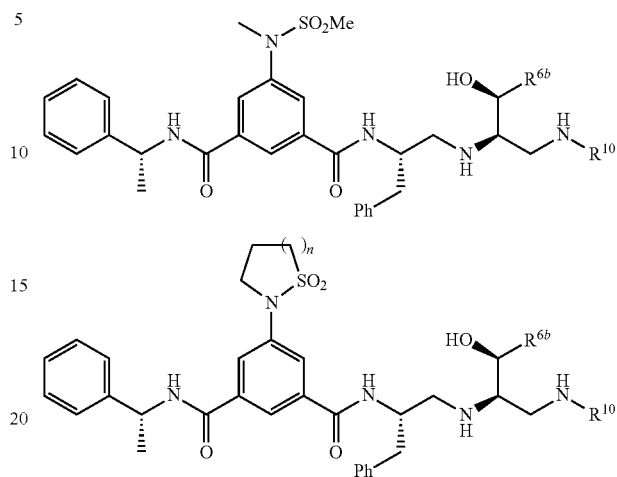

n = 0, 1, 2 are described, wherein $R^{6b}$ and $R^{10}$ are each independently selected in each instance from alkyl, alkylene, heteroalkyl, aryl, alkylaryl, arylalkyl, heteroaryl, heteroarylalkyl, and heterocyclyl, each of which is optionally-substituted.

In another illustrative embodiment, compounds of formulae

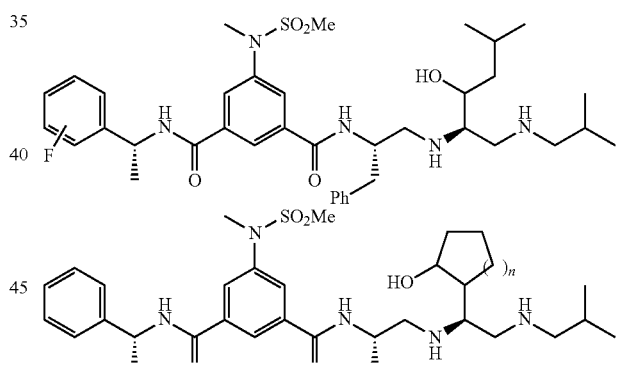

n = 0, 1, 2 are described.

In another embodiment, compounds of formulae

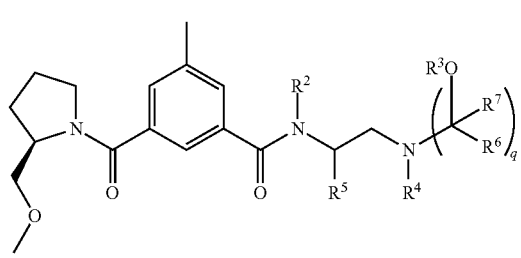

-continued

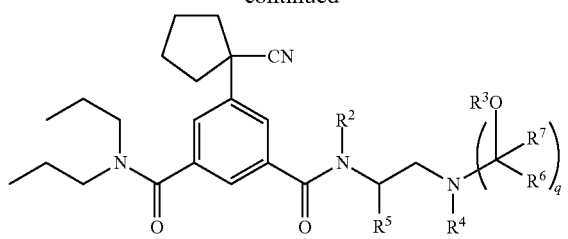

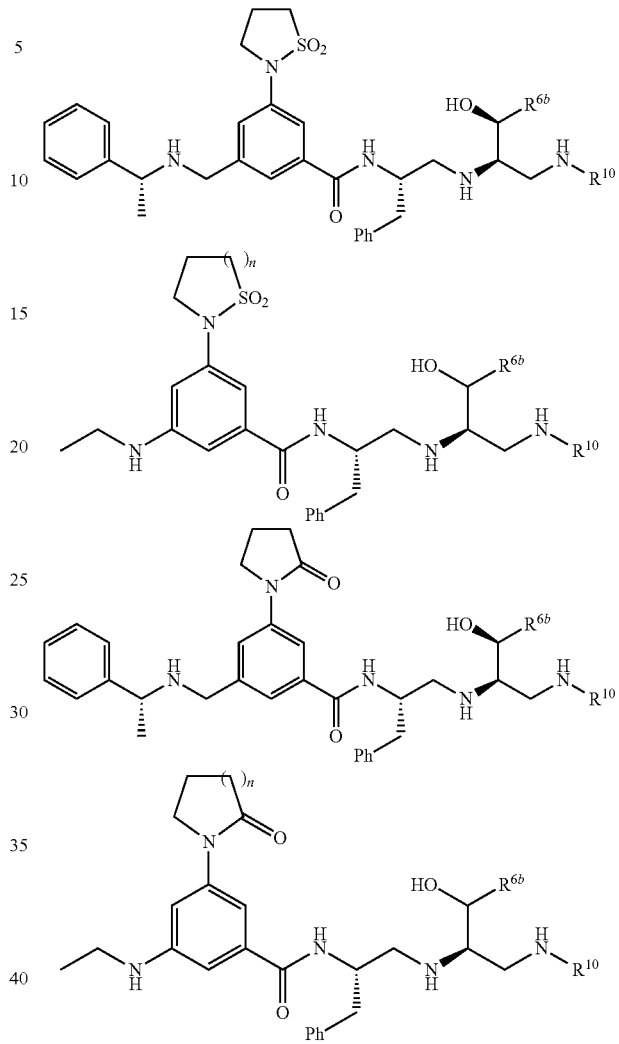

are described; wherein each of R, $R^2$, $R^3$, $R^4$, $R^5$, $R^6$, $R^7$ and q are as described in the various embodiments, and subsets herein.

In another embodiment, compounds of formulae wherein $R^{6b}$ and $R^{10}$ are each independently selected in each instance from alkyl, heteroalkyl, alkylene, aryl, arylalkyl, cycloheteroalkyl (heterocyclyl), heteroaryl, and heteroarylalkyl, each of which is optionally substituted; and n is independently in each instance 0, 1, 2 or 3. In another embodiment, in each instance where $R^{6b}$ and/or $R^{10}$ is alkyl, the alkyl chain of such compounds is optionally substituted with one or more heteroatoms or heterocyclyl groups.

It is also appreciated that in the foregoing embodiments, certain aspects of the compounds are presented in the alternative, such as selections for any one or more of R, $Q^1$, $X^1$, $X^2$, $X^3$, A, $R^1$, $R^2$, $R^3$, $R^4$, $R^5$, $R^6$, $R^{6a}$, $R^{6b}$, $R^{6c}$, $R^7$, $R^8$, $R^9$, $R^{10}$, $R^{11}$, $R^{12}$, $R^{13}$, b, n and q. In one illustrative example R is phenyl, $Q^1$ is 5-N-methylmethylsulfonamido-1,3-phenylene, $X^1$ is ethyl, $X^2$ and $X^3$ are C(O), A is $NR^1$ where $R^1$ is hydrogen, $R^2$, $R^3$, and $R^4$ are hydrogen, $R^5$ is benzyl, $R^{6a}$ is isobutylaminomethyl, and $R^{6b}$ is isobutyl. It is therefore to be understood that various alternate embodiments of the invention include individual members of those lists, as well as the various subsets of those lists. Each of those combinations is to be understood to be described herein by way of the lists.

In each of the foregoing embodiments, the compounds may be prepared using conventional synthetic processes, and/or processes as described herein. In one embodiment, compounds described herein can be prepared by the process shown in the following scheme.

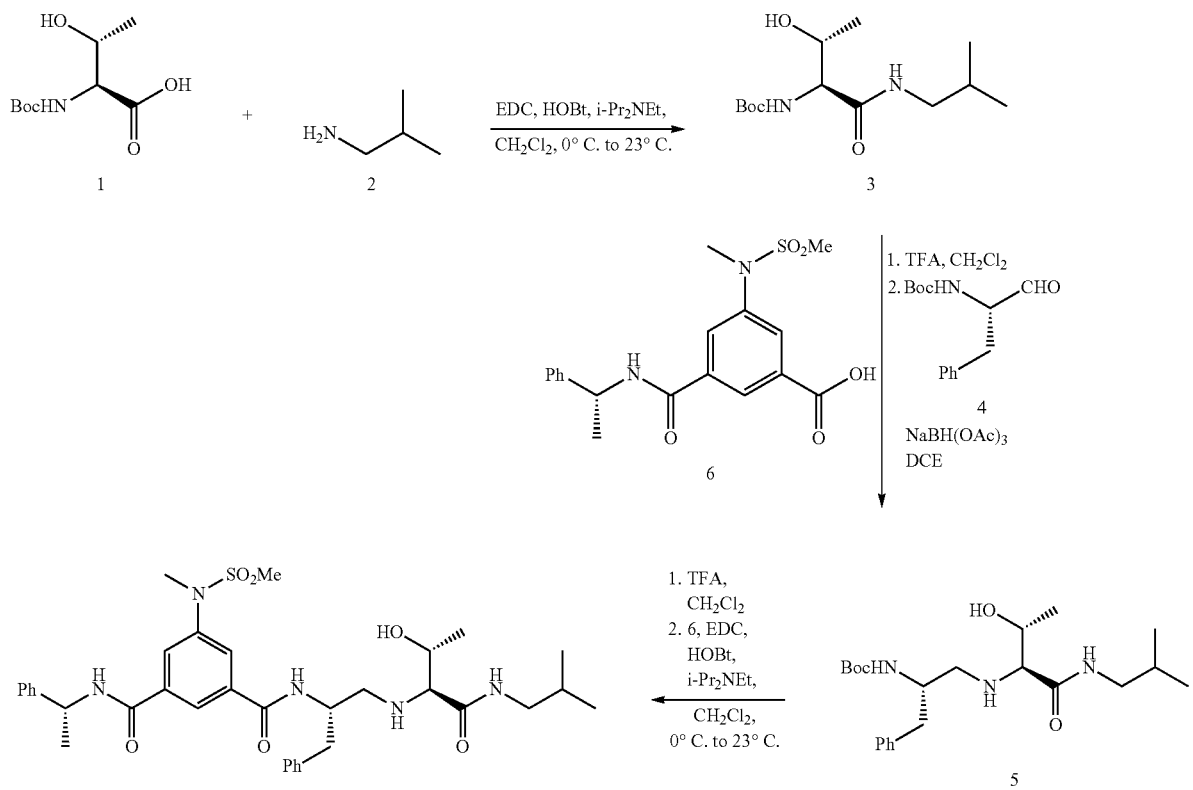
In another embodiment, compounds described herein can be prepared by the process shown in the following scheme.
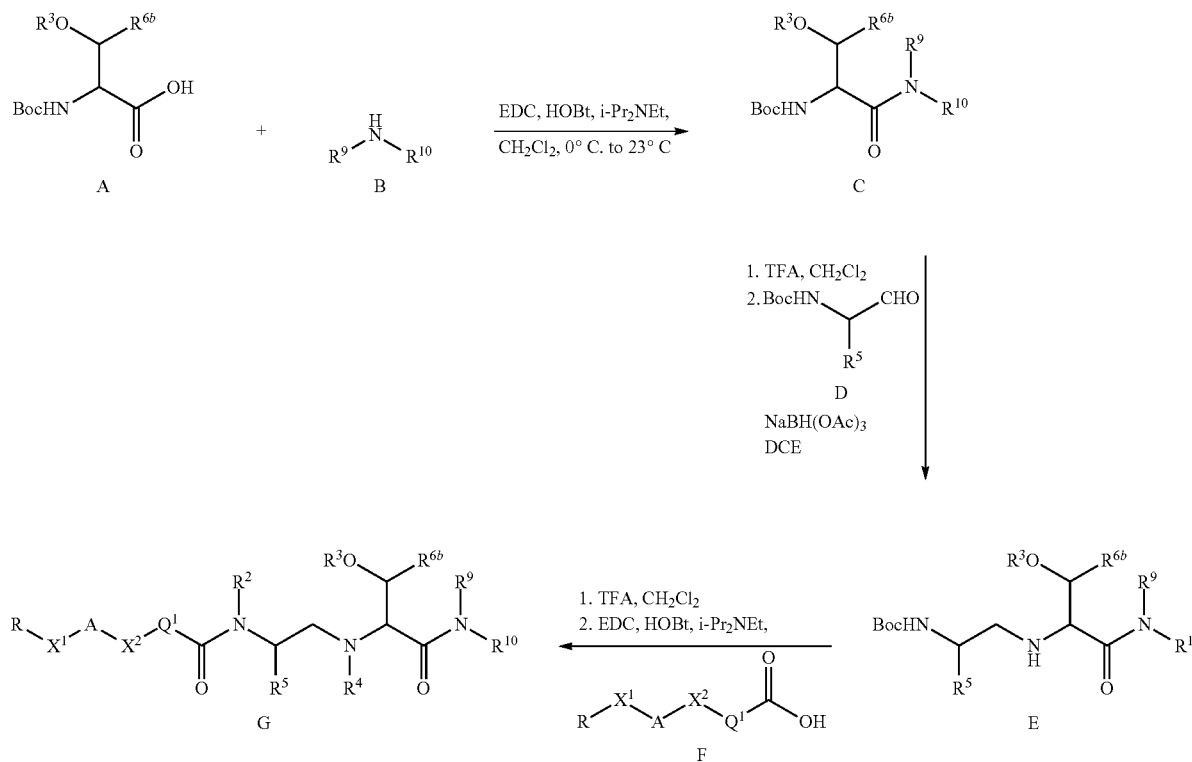

In another embodiment, compounds described herein can be prepared by the process shown in the following scheme.

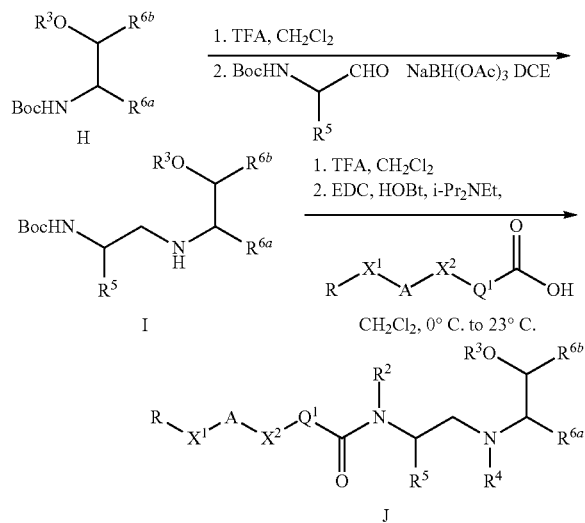

In other embodiments, the starting materials or intermediate compounds may contain additional functional groups. It is appreciated that protecting groups for such functional groups may be required in one or more of the steps in the schemes shown above. Illustrative examples of protecting groups appear in Greene's Protective Groups in Organic Synthesis, 4th Edition, Peter G. M. Wuts and Theodora W. Greene, John Wiley & Sons, Inc., 2006.

The compounds described herein may also be present in the form of a prodrug. It is understood that prodrugs of the compounds described herein may be used in any of the uses of the compounds described herein. The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, ÿ-acetoxyethyl, ÿ-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, ÿ-ethoxycarbonyloxyethyl, ÿ-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, (C$_3$-C$_{20}$)alkanoyl; halo-(C$_3$-C$_{20}$)alkanoyl; (C$_3$-C$_{20}$)alkenoyl; (C$_4$-C$_7$)cycloalkanoyl; (C$_3$-C$_6$)-cycloalkyl(C$_2$-C$_{16}$)alkanoyl; optionally substituted aroyl, such as unsubstituted aroyl or aroyl substituted by 1 to 3 substituents selected from the group consisting of halogen, cyano, trifluoromethanesulphonyloxy, (C$_1$-C$_3$)alkyl and (C$_1$-C$_3$) alkoxy, each of which is optionally further substituted with one or more of 1 to 3 halogen atoms; optionally substituted aryl(C2-C16)alkanoyl, such as the aryl radical being unsubstituted or substituted by 1 to 3 substituents selected from the group consisting of halogen, (C$_1$-C$_3$)alkyl and (C$_1$-C$_3$) alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (C$_1$-C$_3$)alkyl, and (C$_1$-C$_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "alkyl" includes a chain of carbon atoms, which is optionally branched. It is to be understood that alkyl is advantageously of limited length, including $C_1$-$C_{24}$, $C_1$-$C_{12}$, $C_1$-$C_8$, $C_1$-$C_6$, and $C_1$-$C_4$. It is appreciated herein that shorter alkyl groups add less lipophilicity to the compound and accordingly will have different pharmacokinetic behavior.

As used herein, the term "cycloalkyl" includes an optionally branched chain of carbon atoms, where at least a portion of the chain forms one or more rings. In illustrative variations containing two rings, the rings may contain no common atoms, a single common atom, two adjacent common atoms, or more than two common atoms. It is to be understood that chain forming cycloalkyl is advantageously of limited length, including $C_3$-$C_{24}$, $C_3$-$C_{12}$, $C_3$-$C_8$, $C_3$-$C_6$, and $C_3$-$C_4$. It is appreciated herein that shorter alkyl groups add less lipophilicity to the compound and accordingly will have different pharmacokinetic behavior. As used herein, the term "cycloalkenyl" is a cycloalkyl group containing one or more unsaturated bonds.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. Illustrative examples of include alkoxyalkyl, e.g. methoxymethyl and 2-methoxy-ethoxyethyl, alkylthioalkyl, e.g. 2-ethylthio-2-methyl-butyl, alkylaminoalkyl, e.g. 3-aza-pentyl, and the like.

As used herein, the term "cycloheteroalkyl" includes an optionally branched chain of atoms that includes both carbon and at least one heteroatom, where the chain optionally includes one or more unsaturated bonds, and where at least a portion of the chain forms one or more rings. As used herein, it is understood that the term "cycloheteroalkyl" also includes "heterocycloalkyl," "heterocycle," and "heterocyclyl." Illustrative heteroatoms include nitrogen, oxygen, and sulfur. In certain variations, illustrative heteroatoms also include phosphorus, and selenium. Illustrative cycloheteroalkyls include, but are not limited to, tetrahydrofuryl, bis(tetrahydrofuranyl), pyrrolidinyl, tetrahydropyranyl, piperidinyl, morpholinyl, piperazinyl, homopiperazinyl, quinuclidinyl, dihydrofuryl, pyrrollinyl, dihydropyranyl, and the like. It is also to be understood that cycloheteroalkyl includes polycyclic radicals, including fused bicycles, spiro bicycles, and the like.

As used herein, the term "aryl" includes monocyclic and polycyclic aromatic carbocyclic and aromatic heterocyclic groups, each of which may be optionally substituted. As used herein, the term "heteroaryl" includes aromatic heterocyclic groups, each of which may be optionally substituted. Illustrative carbocyclic aromatic groups described herein include, but are not limited to, phenyl, naphthyl, and the like. Illustrative heterocyclic aromatic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "optionally substituted amino" includes derivatives of amino as described herein, such as, but not limited to, acylamino, urea, and carbamate, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, cyano, sulfonic acids and derivatives thereof, carboxylic acids and derivatives thereof, and the like.

The term "optionally substituted aryl" as used herein includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, cyano, sulfonic acids and derivatives thereof, carboxylic acids and derivatives thereof, and the like.

As used herein, pharmaceutically acceptable salts include acid addition salts, base addition salts, and hemisalts. Suitable acid addition salts, include but are not limited to, those formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts, include but are not limited to, those formed from bases which form non-toxic salts. Illustrative examples include the aluminium, arginine, benzathine, calcium, choline, diethylamine, diolamine, glycine, lysine, magnesium, meglumine, olamine, potassium, sodium, tromethamine and zinc salts.

As used herein, references to hemisalts of acids and bases, include but are not limited to, those formed from, for example, hemisulphate and hemicalcium salts.

In another embodiment, a method of treating a patient in need of relief from Alzheimer's disease, the method comprising the step of administering to the patient a therapeutically effective amount of a composition comprising the compound of any one of the preceding embodiments is described.

In another embodiment, compounds of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

As used herein the term "treatment" includes curative, palliative and prophylactic treatment. The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein, and include one or more carriers, diluents, and/or excipients therefor. Such formulation compositions may be administered by a wide variety of conventional routes for the methods described herein, and in a wide variety of dosage formats, utilizing known procedures. See generally, Remington: The Science and Practice of Pharmacy, (21$^{st}$ ed., 2005).

The term "administering" as used herein refers to both local and systemic use, including but not limited to being taken or given orally, parenterally (including by subcutaneous, intramuscular, intravenous and intrathecal routes), by inhalation spray, by nasal, ocular, rectal, sublingual, or buccal routes, or topically, or the like in dosage form unit formulations containing conventional nontoxic pharmaceutically-acceptable carriers, adjuvants and vehicles.

Suitable routes for parenteral administration include intravenous, intraarterial, intraperitoneal, epidural, intraurethral, intrasternal, intramuscular and subcutaneous, as well as any other art recognized route of parenteral administration. Suitable means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier, or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

Examples of emulsifying agents that may be included in the formulations described herein are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Controlled release compositions for oral use may, e.g., be constructed to release the active drug by controlling the dissolution and/or the diffusion of the active drug substance. Illustrative sustained release formulations are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566. The disclosure of each of the foregoing is incorporated herein by reference in its entirety. In addition, the entirety of the disclosure of each of the publications cited herein is also incorporated herein by reference.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

The pharmaceutical compositions described herein may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly (lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(g-lycolic acid) or poly(ortho esters)).

For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

The pharmaceutical compositions may also be administered topically on the skin for percutaneous absorption in dosage forms or formulations containing conventionally nontoxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

It is to be understood that an effective amount of any one or a mixture of the compounds or compositions described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of steroisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

It is appreciated that compounds described herein can exist in unsolvated forms as well as solvated forms, including hydrated forms. It is to be understood that the solvated forms and the unsolvated forms are described herein, either individually or collectively with reference to the compounds and compositions. It is also to be understood that the compounds described herein may exist in multiple amorphous, non-amorphous, partially crystalline, crystalline, and/or other morphological forms. In general, all physical forms are equivalent for the uses contemplated herein and are intended to be included in the methods, uses, compositions, and medicaments described herein. It is also to be understood that the compounds described herein may be present in the form of a salt.

In another embodiment, the compounds described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

METHODS AND EXAMPLES

Example 1

Synthesis of 0657. To a stirring solution of N-Boc-Thr-OH, (1) (342 mg, 1.5 mmol) in $CH_2Cl_2$ (5 mL) at 0° C. was added EDC (358 mg, 1.8 mmol), HOBt (253 mg, 1.8 mmol), isobutylamine (0.16 mL, 1.5 mmol) and i-$Pr_2$Net (0.82 mL, 4.6 mmol), the resulting mixture was stirred for 16 h at 23° C. The reaction mixture was then concentrated in vacuo and the resulting residue was subjected to column chromatography (5:95) to give the amide (3) (321 mg, 78%) as a colorless oil.

To the solution of amide (3) (80 mg, 0.29 mmol) in $CH_2Cl_2$ (1 mL) at 0° C. was added 30% trifluoroacetic acid in $CH_2Cl_2$ (1.5 mL) and the reaction was stirred for 40 min. The solvent was then removed under reduced pressure and the residue was dissolved in 1,2-dichloroethane (3 mL). To this solution was added Boc-protected phenylalanal, (4) (72 mg, 0.29 mmol) followed by NaBH(Oac)$_3$ (122 mg, 0.58 mmol) and the resulting mixture was stirred at 23° C. for 12 h. The reaction was then quenched with sat. $NaHCO_3$, the aqueous layer was extracted with $CH_2Cl_2$. The organic layer was then concentrated under reduced pressure and the resulting residue was subjected to column chromatography to give amine (5) (78 mg, 66%) as a colorless oil.

To the solution of amine (5) (33 mg, 0.08 mmol) in CH$_2$Cl$_2$ (1 mL) at 0° C. was added 30% trifluoroacetic acid in CH$_2$Cl$_2$ (1.5 mL) and the reaction was stirred for 40 min. The solvent was removed under reduced pressure and the residue was dissolved in CH$_2$Cl$_2$ (1 mL). The amine thus obtained was added to a stirring mixture of acid (6) (30 mg, 0.8 mmol) (Ghosh A. K.; Kumaragurubaran, N.; Hong, L.; Kulkarni, S. S.; Xu, X.; Chang, W.; Weerasena, V.; Turner, R.; Koelsch, G.; Bilcer, G.; Tang, J. *J. Med. Chem.* 50:2399-2407 (2007)), EDC (35 mg, 0.18 mmol), HOBt (24 mg, 0.18 mmol) followed by i-Pr$_2$Net (0.14 mL, 0.8 mmol) and the resulting mixture was stirred for 16 h at 23° C. The reaction mixture was concentrated in vacuo and the resulting residue was purified by column chromatography (5:95, MeOH, CHCl$_3$) to give the title compound (0657) (40 mg, 75% yield) as a white solid.

Example 2

Inhibition of BACE1 (Memapsin 2). Potency of compounds are determined by measurement of their inhibition of memapsin 2 catalytic activity toward a fluorescent substrate. Kinetic inhibition experiments are performed using the procedure as described in Ermolieff, et al. (Biochemistry 39:12450-12456 (2000), the teachings of which are incorporated hereby in their entirety). Briefly, assays are performed at pH 4, 37° C., by pre-incubation of memapsin 2 enzyme with compound for 20 minutes. Activity measure is initiated by addition of a fluorogenic substrate FS-2 (Bachem Americas, Torrance, Calif.). Fluorescent signal increase over time is measured as a rate of hydrolysis of the peptide substrate. Inhibition of hydrolytic rate is expressed relative to uninhibited controls and fit to a model for tight-binding inhibitors (J. Bieth, in "Proteinase Inhibitors," Bayer Symposium V, 463-469, 1974).

Example 3

Inhibition of Memapsin 1, Memapsin 2, and Cathepsin D Catalytic Activity. A substrate peptide H$_3$N-ELDLAVEF-WHDR-CO$_2$ (SEQ ID NO: 1) (used for inhibition assay of memapsin 2, memapsin 1, and cathepsin D) is dissolved at 2 mg/ml in DMSO and diluted 1:100 in 0.1 M sodium acetate, pH 4.0 just prior to assay. Inhibitor dissolved in DMSO is diluted into 0.1 M sodium acetate, pH 4.0 (1:100 dilution). A 50 µL aliquot of the inhibitor solution in pH 4 buffer is combined with 150 µL of 0.1 M sodium acetate containing 100-200 nM of memapsin 1, memapsin 2, or cathepsin D. Following a pre-incubation at 37° C., the proteolytic assay is initiated by addition of 50 µL of the substrate diluted into pH 4 buffer, and incubation continued at 37° C. Aliquots are removed at time intervals, and combined with an equal volume of MALDI-TOF matrix (α-hydroxycinnamic acid in acetone, 20 mg/mL) and immediately spotted in duplicate onto a stainless-steel MALDI sample plate. MALDI-TOF mass spectrometry is performed on a PE Biosystems Voyager DE instrument. The instrument is operated at 25,000 accelerating volts in positive mode with a 150 ns delay. Ions with a mass-to-charge ratio (m/z) are detected in the range of 650-2000 atomic mass units. Data are analyzed by the Voyager Data Explorer module to obtain ion intensity data for mass species of substrates and corresponding products in a given mixture. Relative product formation is calculated as the ratio of signal intensity of the product to the sum of signal intensities of both product and the corresponding substrate. Relative product formed per unit time is obtained from non-linear regression analysis of the data representing the initial 15% formation of product using the model:

$$1-e^{-kT}$$

where k is the relative hydrolytic rate constant and T was time in seconds. Alternatively, relative hydrolytic rates are determined using a fluorogenic cleavage assay (Ermolieff, J. et al., *Biochemistry*, 39: 12450-12456 (2000)). Initial rates from either method were expressed relative to uninhibited controls and the inhibition constant K$_i$ was determined by a non-linear fit to a tight-binding model of competitive inhibition (Bieth, J., *Bayer—Symposium V. Proteinase Inhibitors*, pp 463-469, Spinger-Varlag, Berlin (1994)). Results are shown in Cellular Aβ IC$_{50}$ Determinations.

The potency of compounds against memapsin 2 catalytic activity is determined in a cellular assay of Aβ production. Compounds that successfully penetrate the cell membrane demonstrate their ability to inhibit memapsin 2 catalytic activity in endosomal compartments, thus blocking the production of Aβ. Chinese hamster ovary cells that over-express human APP695 with the London and Swedish mutations are seeded in multi-well plates at 10% confluency. Compounds are dissolved in DMSO to concentrations near 1 mM, and diluted into culture media to a final concentration near 4 µM (final 0.4% DMSO). Compounds are diluted serially and applied to cells in multi-well plates 48 h after seeding. Incubation is continued in 5% CO$_2$ at 37 degrees C. for 24 h. Aliquots are removed and assayed for Aβ$_{40}$ content using a sandwich ELISA (BioSource International). Amount of Aβ$_{40}$ over the range of concentration of compounds, relative to control incubations, are fit to a 4-parameter IC$_{50}$ model.

Example 4

Illustrative inhibition constants of BACE1 for the compounds described herein are shown in the following TABLE.

| Example | Structure | MW | Activity K$_i$ (a) |
|---|---|---|---|
| 0397 | 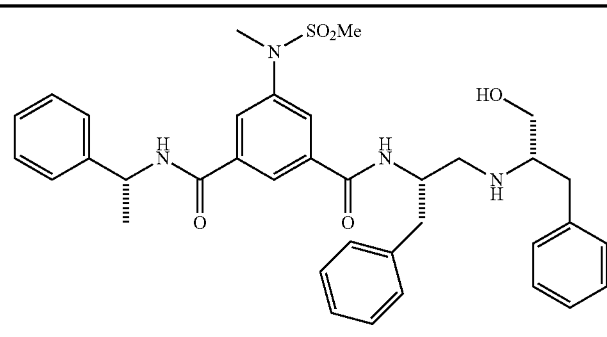 | 643 | + |

-continued

| Example | Structure | MW | Activity $K_i$ (a) |
|---|---|---|---|
| 0407 | 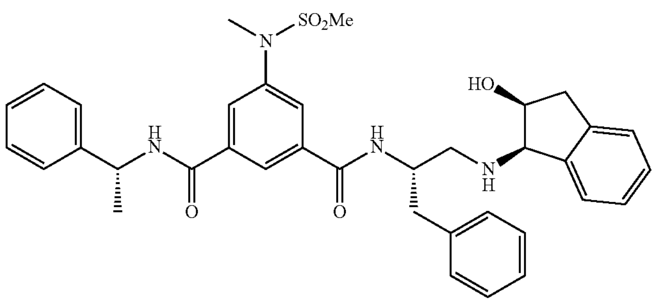 [SMILES: C[C@@H](NC(=O)c1cc(C(=O)N[C@H](CN[C@@H]2c3ccccc3C[C@@H]2O)Cc2ccccc2)cc(N(C)S(C)(=O)=O)c1)c1ccccc1] | 641 | + |
| 0417 | 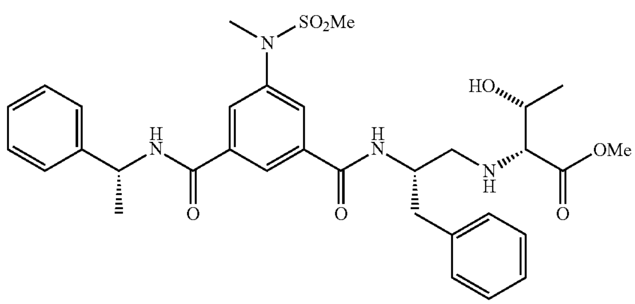 [SMILES: COC(=O)[C@H](NC[C@H](Cc1ccccc1)NC(=O)c1cc(C(=O)N[C@H](C)c2ccccc2)cc(N(C)S(C)(=O)=O)c1)[C@@H](C)O] | 625 | + |
| 0427 | 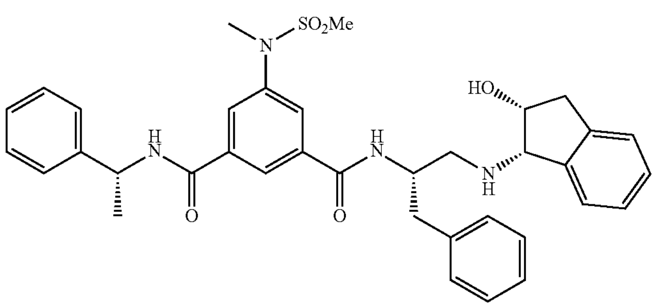 [SMILES: C[C@@H](NC(=O)c1cc(C(=O)N[C@H](CN[C@H]2c3ccccc3C[C@H]2O)Cc2ccccc2)cc(N(C)S(C)(=O)=O)c1)c1ccccc1] | 641 | + |
| 0637 | 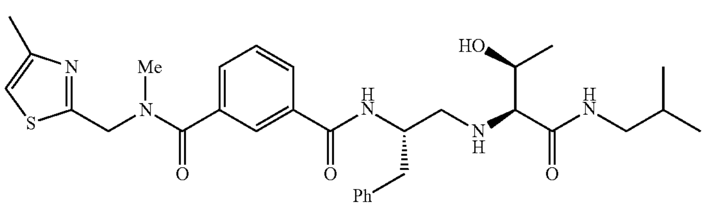 [SMILES: Cc1csc(CN(C)C(=O)c2cccc(C(=O)N[C@H](CN[C@H](C(=O)NCC(C)C)[C@H](C)O)Cc3ccccc3)c2)n1] | 580 | + |
| 0647 | 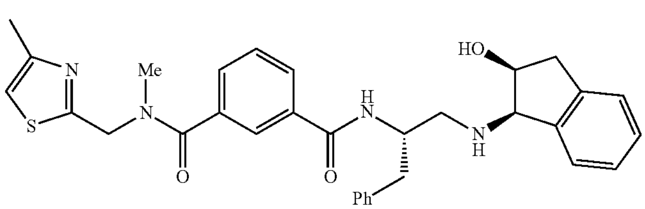 [SMILES: Cc1csc(CN(C)C(=O)c2cccc(C(=O)N[C@H](CN[C@@H]3c4ccccc4C[C@@H]3O)Cc3ccccc3)c2)n1] | 555 | + |
| 0657 | 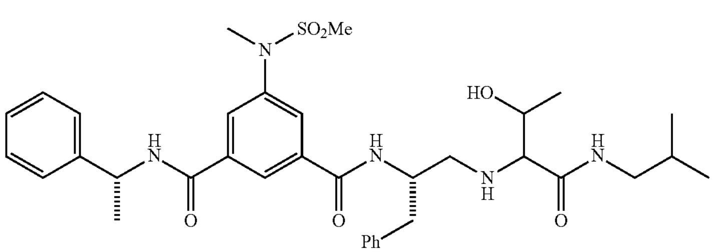 [SMILES: CC(C)CNC(=O)C(NC[C@H](Cc1ccccc1)NC(=O)c1cc(C(=O)N[C@H](C)c2ccccc2)cc(N(C)S(C)(=O)=O)c1)C(C)O] | 666 | ++ |

| Example | Structure | MW | Activity K$_i$ (a) |
|---|---|---|---|
| 0667 | 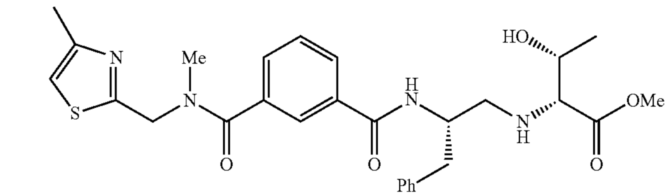 [SMILES: COC(=O)[C@H](NC[C@H](Cc1ccccc1)NC(=O)c1cccc(C(=O)N(C)Cc2nc(C)cs2)c1)[C@@H](C)O] | 539 | − |
| 0439 | 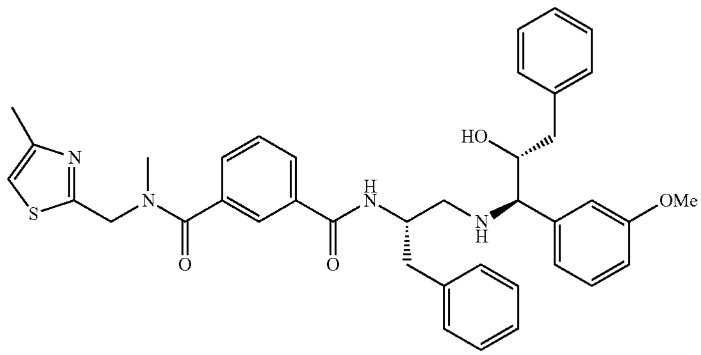 [SMILES: COc1cccc([C@@H](NC[C@H](Cc2ccccc2)NC(=O)c2cccc(C(=O)N(C)Cc3nc(C)cs3)c2)[C@H](O)Cc2ccccc2)c1] | 663 | − |
| 0449 | 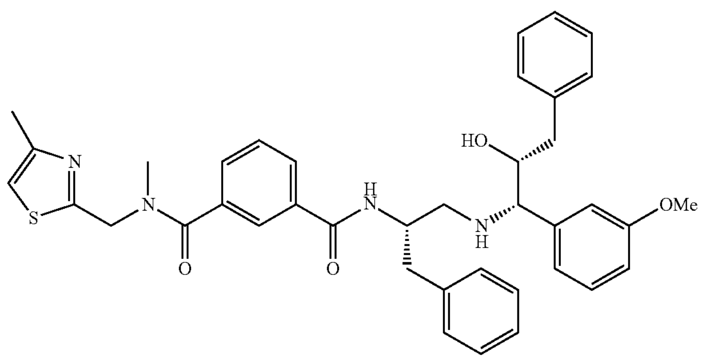 [SMILES: COc1cccc([C@H](NC[C@H](Cc2ccccc2)NC(=O)c2cccc(C(=O)N(C)Cc3nc(C)cs3)c2)[C@H](O)Cc2ccccc2)c1] | 663 | − |
| 0539 | 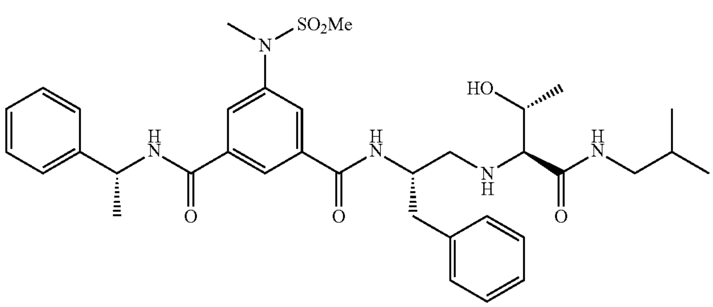 [SMILES: CC(C)CNC(=O)[C@@H](NC[C@H](Cc1ccccc1)NC(=O)c1cc(C(=O)N[C@H](C)c2ccccc2)cc(N(C)S(C)(=O)=O)c1)[C@@H](C)O] | 666 | +++ |
| 0549 | 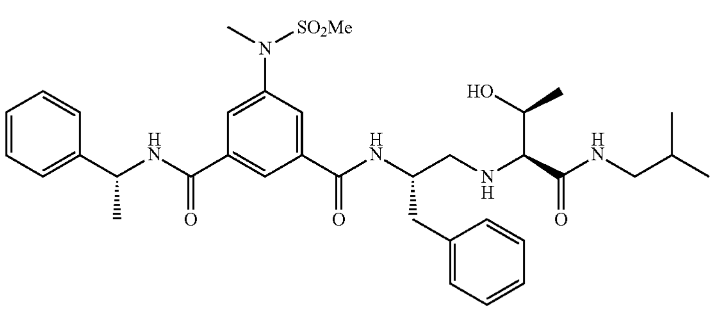 [SMILES: CC(C)CNC(=O)[C@@H](NC[C@H](Cc1ccccc1)NC(=O)c1cc(C(=O)N[C@H](C)c2ccccc2)cc(N(C)S(C)(=O)=O)c1)[C@H](C)O] | 666 | ++ |

| Example | Structure | MW | Activity $K_i$ (a) |
|---|---|---|---|
| 1439 | 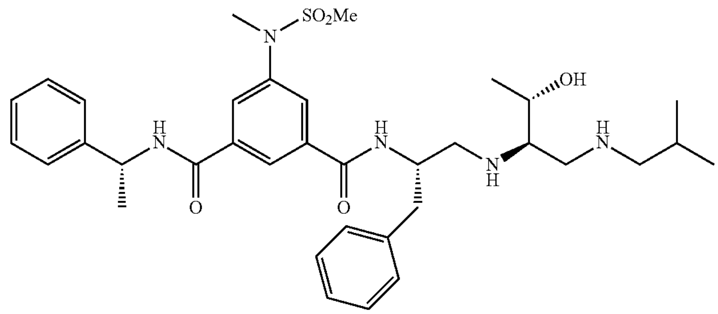 [SMILES: CC(C)CNC[C@@H](NC[C@H](Cc1ccccc1)NC(=O)c1cc(C(=O)N[C@H](C)c2ccccc2)cc(N(C)S(C)(=O)=O)c1)[C@H](C)O] | 652 | +++ |
| 1479 | 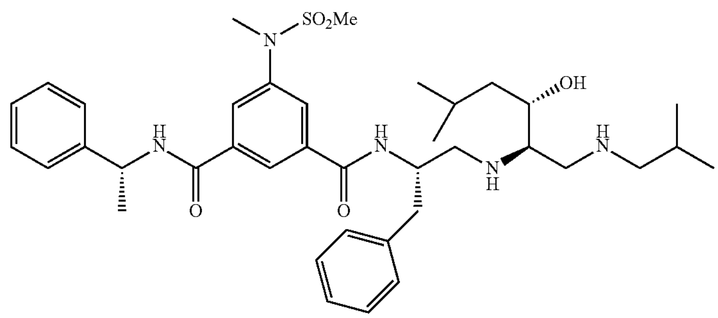 [SMILES: CC(C)CNC[C@@H](NC[C@H](Cc1ccccc1)NC(=O)c1cc(C(=O)N[C@H](C)c2ccccc2)cc(N(C)S(C)(=O)=O)c1)[C@@H](O)CC(C)C] | 694 | +++ |

(a) >1 mM, (−); <1 mM, (+); <10 μM, (++); <100 nM, (+++).

While certain embodiments of the present invention have been described and/or exemplified above, it is contemplated that considerable variation and modification thereof are possible. Accordingly, the present invention is not limited to the particular embodiments described and/or exemplified herein.

What is claimed is:

1. A compound of formula

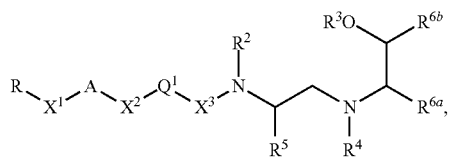

or a pharmaceutically acceptable salt, isomer, mixture of isomers, crystalline form, non crystalline form, hydrate, or solvate thereof, wherein R is optionally substituted aryl, $X^1$ is optionally substituted alkylene, and A is $NR^1$, where $R^1$ is hydrogen or alkyl; or R is optionally substituted heteroaryl, $X^1$ is $CH_2$, A is $NR^1$, and $R^1$ is hydrogen or alkyl; or A is $NR^1$, R is heteroaryl, and $R^1$, $X^1$ and the attached nitrogen form a heterocycle;

$X^2$ is C(O);

$Q^1$ is 1,3-phenylene, which is optionally substituted at the 5-position with N-methylmethylsulfonylamido, alkyl, or heteroalkyl;

$X^3$ is C(O);

$R^2$, $R^3$, and $R^4$ are each hydrogen;

$R^5$ is arylalkyl, which is optionally substituted;

$R^{6a}$ is $C(O)NHR^{10a}$, where $R^{10a}$ is alkyl; and $R^{6b}$ is alkyl.

2. The compound of claim 1 which is the most potent isomer of diastereoisomers formed by $R^{6a}$ and $R^{6b}$ in the inhibition of BACE1.

3. The compound of claim 1 wherein R is optionally substituted aryl, $X^1$ is optionally substituted alkylene, and A is $NR^1$, where $R^1$ is hydrogen or alkyl.

4. The compound of claim 3 wherein $R^1$ is hydrogen.

5. The compound of claim 3 wherein R is aryl, $X^1$ is alkylene, and $R^1$ is hydrogen.

6. The compound of claim 1 wherein R is optionally substituted heteroaryl, $X^1$ is $CH_2$, A is $NR^1$, and $R^1$ is hydrogen or alkyl.

7. The compound of claim 6 wherein the heteroaryl is optionally substituted oxazolyl or thiazolyl.

8. The compound of claim 1 wherein A is $NR^1$, R is heteroaryl, and $R^1$, $X^1$ and the attached nitrogen form a heterocycle.

9. The compound of claim 8 wherein the heterocycle is pyrrolidinyl.

10. The compound of claim 1 which is a compound of formula

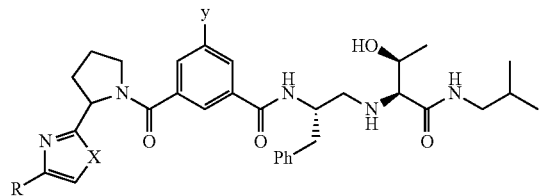

wherein X is O, S, or NMe; R is hydrogen, alkyl, or heteroalkyl; and y is hydrogen, alkyl, or heteroalkyl.

11. The compound of claim 1 wherein A is $NR^1$, where $R^1$ is hydrogen; and $R—X^1—$ form (R)-1-phenyl-1-ethyl.

12. The compound of claim 1 which is a compound of formula

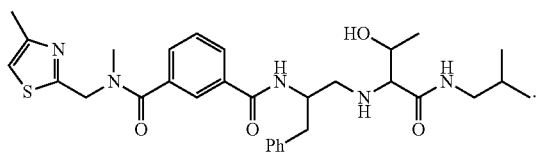 [SMILES: Cc1csc(CN(C)C(=O)c2cccc(C(=O)NC(CNC(C(=O)NCC(C)C)C(C)O)Cc3ccccc3)c2)n1]

13. A pharmaceutical composition comprising the compound of claim 1, or a pharmaceutically acceptable salt thereof, and a pharmaceutically acceptable carrier or excipient.

* * * * *

```
                        SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Enzyme assay substrate

<400> SEQUENCE: 1

Glu Leu Asp Leu Ala Val Glu Phe Trp His Asp Arg
1               5                   10
```